(12) United States Patent
Buck et al.

(10) Patent No.: US 10,349,878 B2
(45) Date of Patent: *Jul. 16, 2019

(54) ELECTROCHEMICAL SENSOR HAVING SYMMETRICALLY DISTRIBUTED ANALYTE SENSITIVE AREAS

(71) Applicant: Roche Diabetes Care, Inc., Indianapolis, IN (US)

(72) Inventors: Harvey Buck, Indianapolis, IN (US); Georgeta Lica, Indianapolis, IN (US); Karl-Heinz Koelker, Gruenstadt (DE); Ewald Rieger, Bobenheim-Roxheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/700,392

(22) Filed: Sep. 11, 2017

(65) Prior Publication Data

US 2017/0367628 A1 Dec. 28, 2017

Related U.S. Application Data

(63) Continuation of application No. 14/803,770, filed on Jul. 20, 2015, now Pat. No. 9,757,060, which is a
(Continued)

(51) Int. Cl.
*A61B 5/05* (2006.01)
*A61B 5/1477* (2006.01)
(Continued)

(52) U.S. Cl.
CPC .......... *A61B 5/1477* (2013.01); *A61B 5/1473* (2013.01); *G01N 27/327* (2013.01); *A61B 2560/0468* (2013.01); *A61B 2562/043* (2013.01)

(58) Field of Classification Search
CPC . A61B 5/1473; A61B 5/1468; A61B 5/14532; A61B 2560/0468; A61B 2562/0209; G01N 27/327; G01N 33/5438
See application file for complete search history.

(56) References Cited

U.S. PATENT DOCUMENTS 4,655,880 A 4/1987 Liu
6,212,416 B1 4/2001 Ward et al.
(Continued)

FOREIGN PATENT DOCUMENTS

EP 2 163 190 A1 3/2010
WO WO 98/42252 A1 10/1998
(Continued)

*Primary Examiner* — Christian Jang
(74) *Attorney, Agent, or Firm* — Bose McKinney & Evans LLP

(57) ABSTRACT

The present invention provides an electrochemical sensor that employs multiple electrode areas that are exposed for contact with a body fluid, e.g., when the sensor is inserted subcutaneously into a patient's skin. The exposed electrode areas are arranged symmetrically, such that a symmetrical potential distribution is produced when an AC signal is applied to the sensor. The sensors in accordance with these teachings can advantageously be used with AC signals to determine characteristics of the sensor and thus improve sensor performance. These teachings also provide a biocompatible sensor with multiple reference electrode areas that are exposed for contact with body fluid.

18 Claims, 15 Drawing Sheets

Related U.S. Application Data continuation of application No. 12/901,078, filed on Oct. 8, 2010, now Pat. No. 9,084,570.

(51) Int. Cl.
   *G01N 27/327* (2006.01)
   *A61B 5/1473* (2006.01)

(56) References Cited

U.S. PATENT DOCUMENTS

| | | |
|---|---|---|
| 8,060,174 B2 | 11/2011 | Simpson et al. |
| 9,084,570 B2 * | 7/2015 | Buck .................... A61B 5/1473 |
| 9,757,060 B2 * | 9/2017 | Buck .................... A61B 5/1473 |
| 2002/0188185 A1 | 12/2002 | Sohrab |
| 2007/0027384 A1 | 2/2007 | Brister et al. |
| 2007/0135698 A1 | 6/2007 | Shah et al. |
| 2007/0170073 A1 | 7/2007 | Wang et al. |
| 2007/0299617 A1 | 12/2007 | Willis |
| 2008/0039702 A1 | 2/2008 | Hayter et al. |
| 2008/0214910 A1 | 9/2008 | Buck |
| 2009/0198117 A1 | 8/2009 | Cooper et al. |
| 2009/0242425 A1 | 10/2009 | Kamath et al. |
| 2009/0292188 A1 | 11/2009 | Hoss et al. |
| 2010/0025238 A1 | 2/2010 | Gottlieb et al. |
| 2010/0081906 A1 | 4/2010 | Hayter et al. |
| 2010/0113907 A1 | 5/2010 | Schwind et al. |
| 2011/0196216 A1 | 8/2011 | Quarder et al. |
| 2016/0054424 A1 | 2/2016 | Yang et al. |

FOREIGN PATENT DOCUMENTS

| | | |
|---|---|---|
| WO | WO 2007/079015 A2 | 7/2007 |
| WO | WO 2010/028708 A1 | 3/2010 |

* cited by examiner

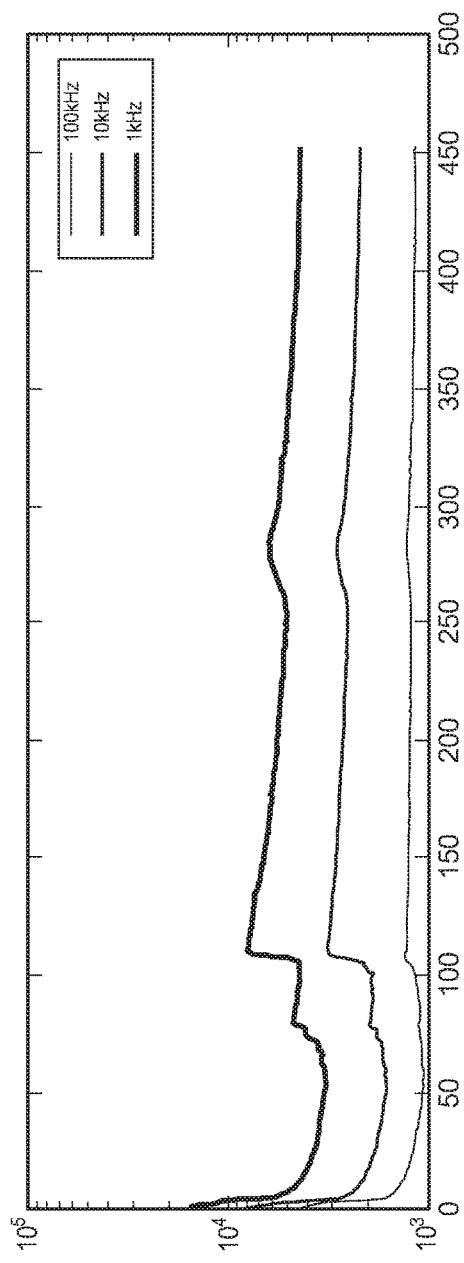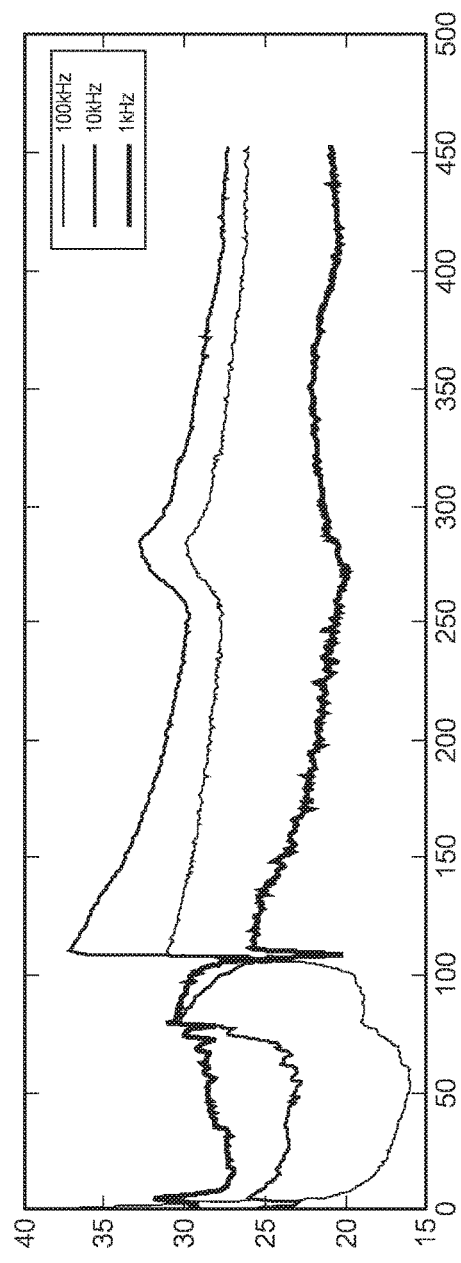

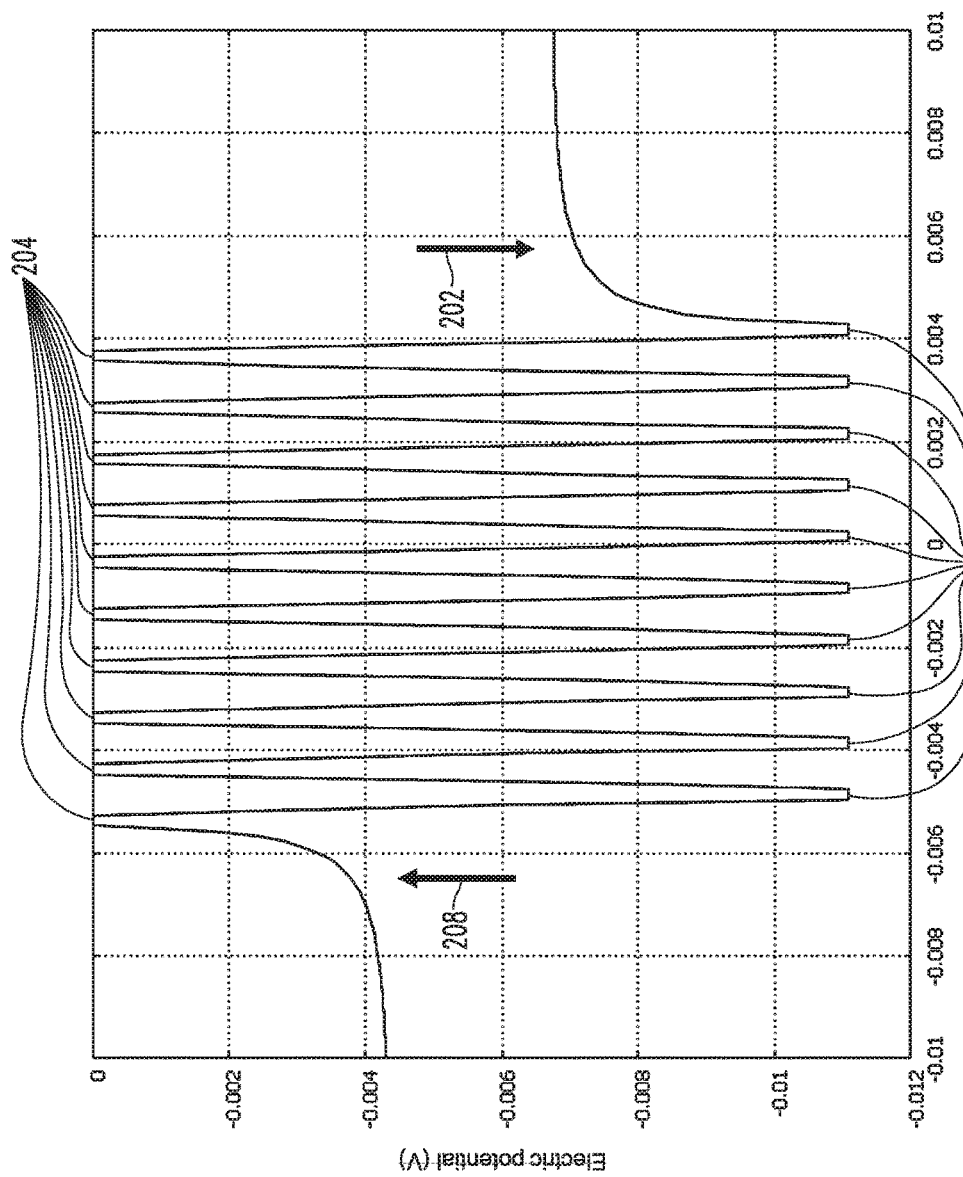

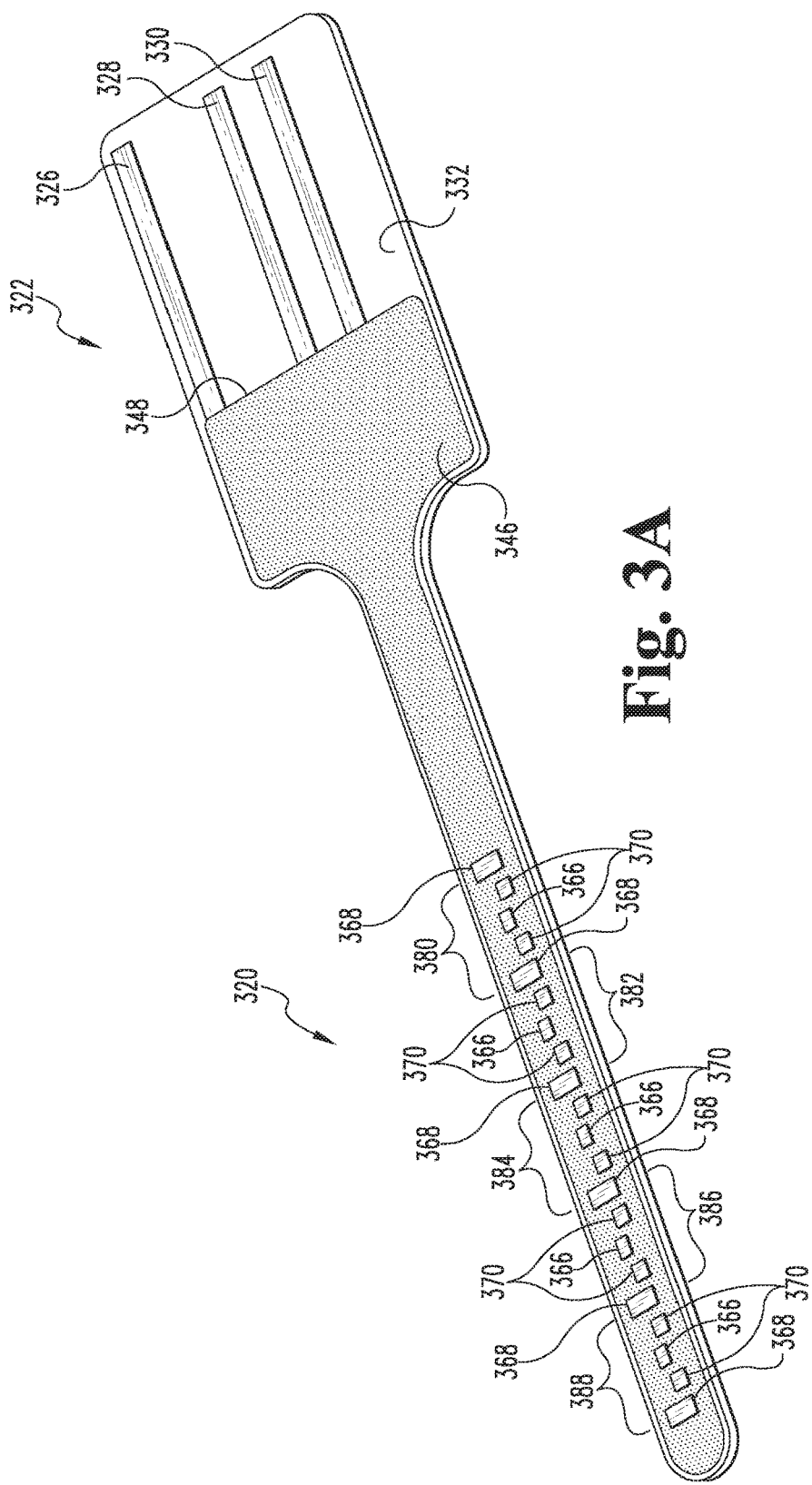

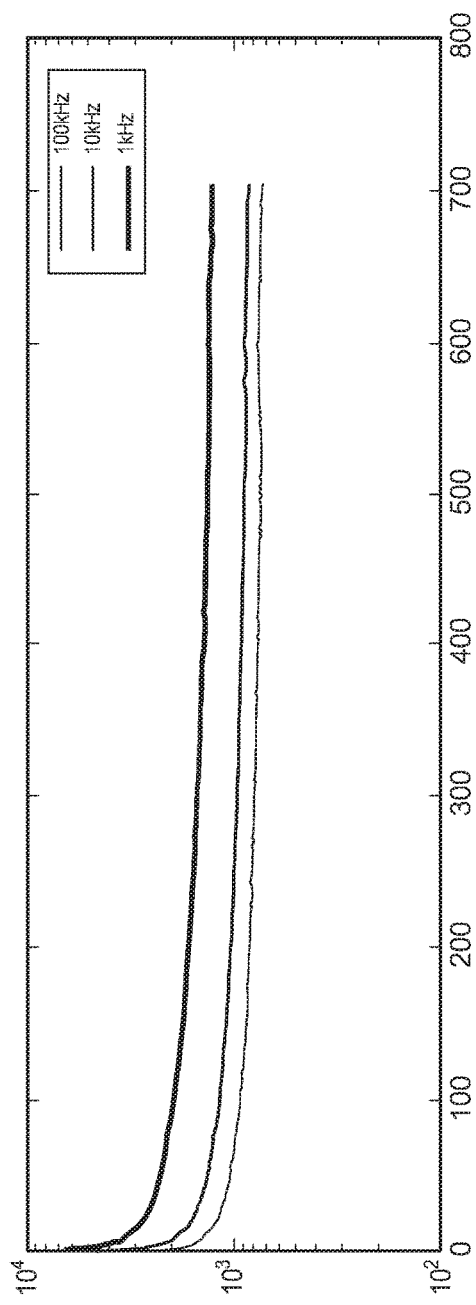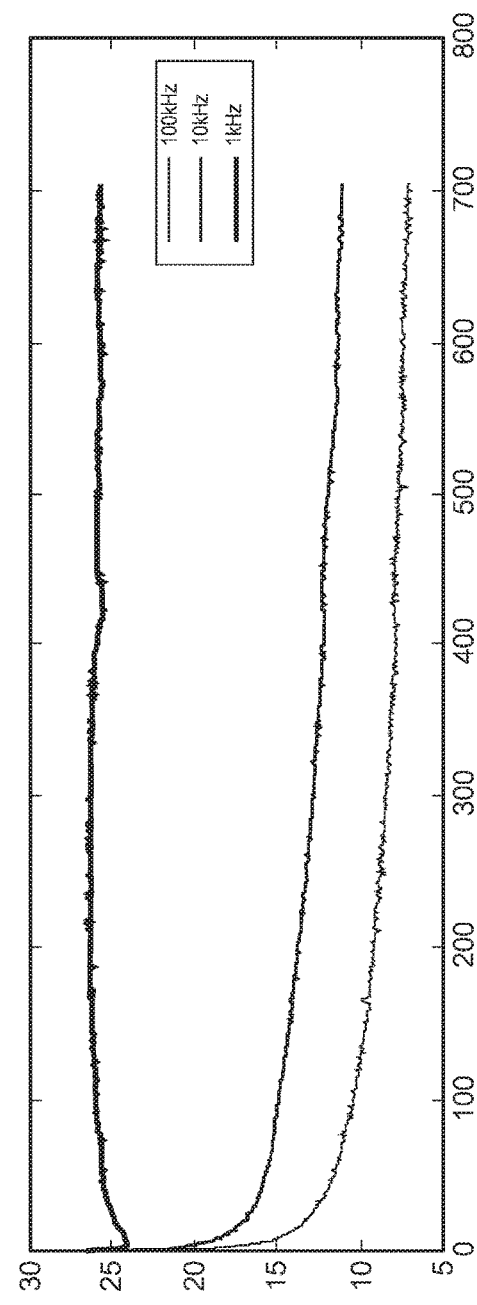

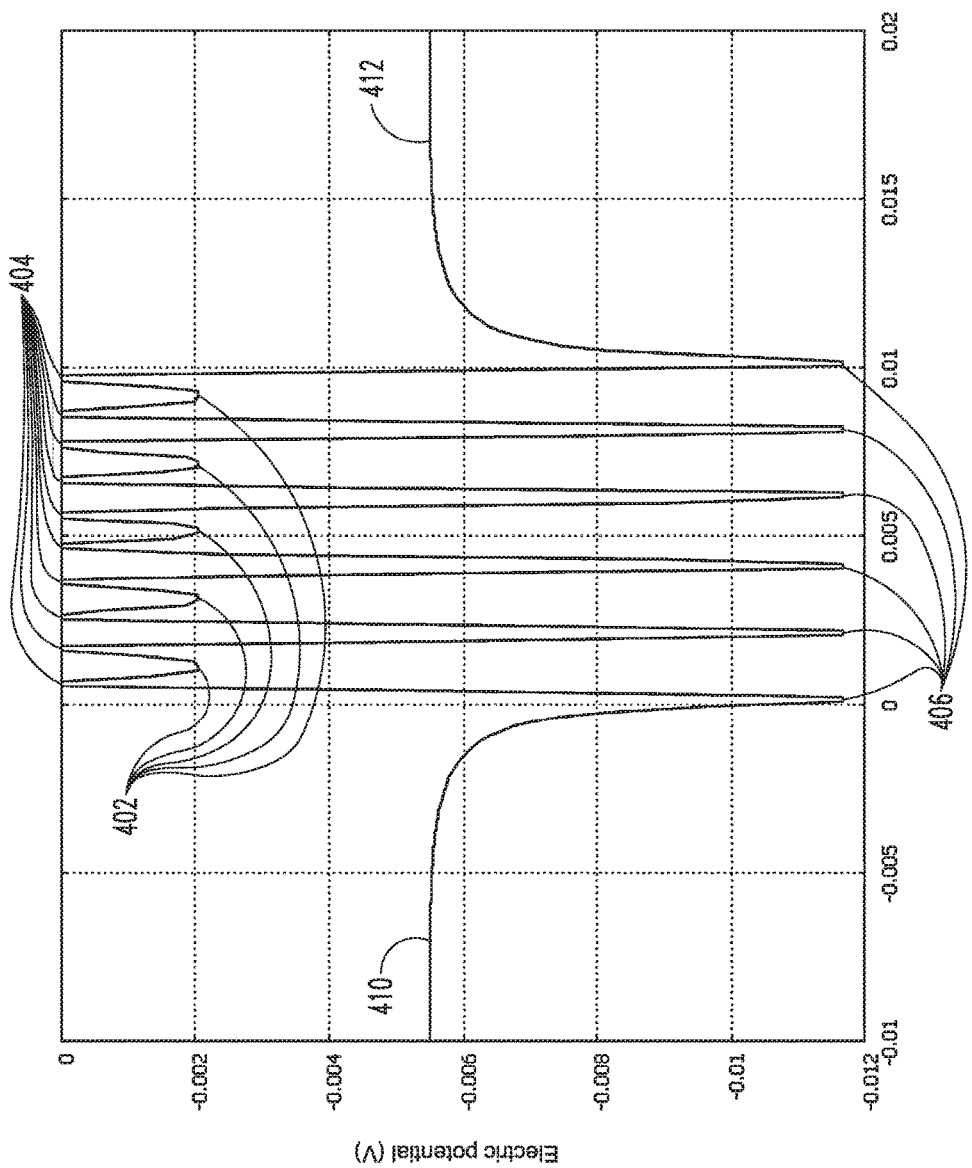

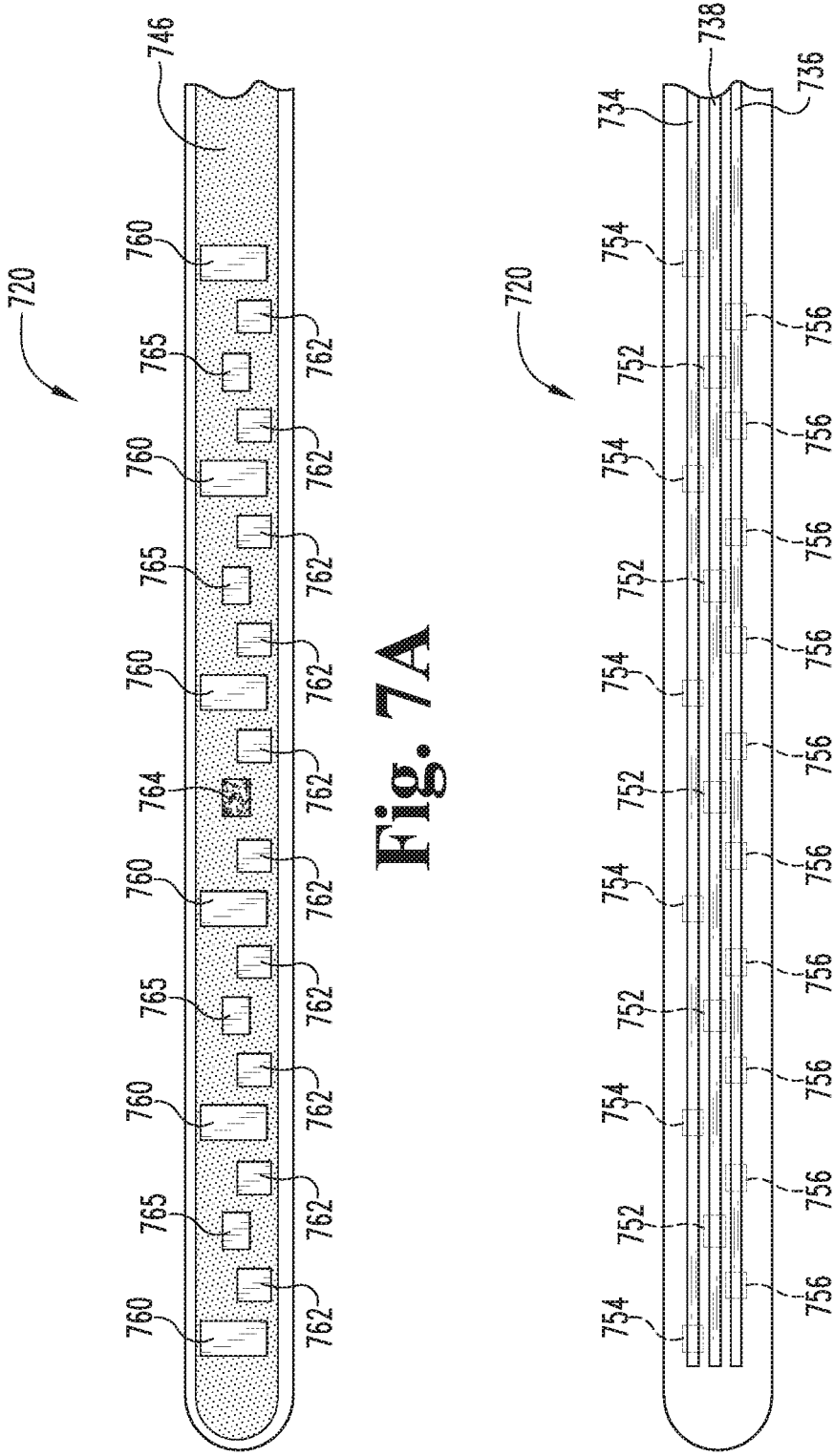

ELECTROCHEMICAL SENSOR HAVING SYMMETRICALLY DISTRIBUTED ANALYTE SENSITIVE AREAS

RELATED APPLICATIONS

This application is a continuation of U.S. patent application Ser. No. 14/803,770, filed Jul. 20, 2015, which is a continuation application of U.S. patent application Ser. No. 12/901,078, filed Oct. 8, 2010, each of which are incorporated herein by reference in their entireties.

BACKGROUND

The present invention relates to in vivo measurement. More specifically, the present invention relates to sensing, and sensors for sensing, the concentration of particular substances in body fluids.

Measurement of the concentration of particular chemicals in body fluids is useful for many types of medical diagnosis and treatment. Insulin-dependent diabetic patients, for example, might measure the concentration of glucose in their blood multiple times per day, and electrochemical sensors for in vivo measurements of glucose are known. Such sensors typically have a portion that can be inserted into tissue and include one or more electrodes that come into contact with interstitial fluid after insertion. Electronic circuitry external to the human is used to control operation of the sensor by sending electrical signals to sensor electrodes and monitoring an electrochemical reaction that takes place between the fluid/tissue and the electrodes.

One problem with in vivo sensors that are used for continuous monitoring is that the physical and/or chemical characteristics of the sensor as well as the histology of the tissue surrounding the implantation site change over time. For example, the capacitance of the sensor may change, an electrically conductive path of the sensor may fail, or the permeability of one or more membranes in the sensor can change. Similarly, migration of leukocytes and fibrin depositing in the environment containing the analyte can change the electrical conductivity of the environment of the sensor, for example. U.S. Publication No. 2008/0214910, which is hereby incorporated herein by reference, teaches applying an AC input signal to the electrodes of a sensor and monitoring an AC output signal thereby produced. A complex impedance of the sensor based on these AC signals can be determined, from which information concerning the changing characteristics of the sensor can be determined. Sensor performance can thus be improved.

In spite of improvements such as disclosed by U.S. Publication No. 2008/0214910, in vivo sensors remain limited in durability, accuracy, ease of manufacture, and potential lifetime in use. There is thus a need for improved in vivo sensors and sensing techniques.

SUMMARY

The present invention provides an electrochemical sensor that employs multiple exposed analyte sensitive electrode areas that are arranged symmetrically relative to one another, whereby a symmetrical potential distribution is produced when an alternating current is applied to the sensor. The sensors in accordance with these teachings can advantageously be used with AC signals to determine characteristics of the sensor and thus improve sensor performance. These teachings also provide a biocompatible sensor with multiple exposed reference electrode areas.

In one embodiment, an electrochemical sensor for in vivo use is provided. The sensor comprises a substrate, a working electrode formed on or in the substrate and having multiple working electrode areas exposed for contact with a body fluid. The sensor also includes a second electrode formed on or in the substrate and having at least one second electrode area exposed for contact with a body fluid. The multiple working electrode areas and the at least one second electrode area are arranged symmetrically relative to each other, such that a symmetrical potential distribution is obtained when an alternating current is applied to the sensor.

The sensor may further be configured such that the at least one second electrode area comprises multiple second electrode areas. More particularly, the second electrode may comprise a reference electrode and the multiple second electrode areas may comprise reference electrode areas exposed for contact with body fluid. Further, the sensor may also include a counter electrode formed on or in the substrate, the counter electrode comprising at least one counter electrode area exposed for contact with body fluid. In some embodiments, the counter electrode may have multiple counter electrode areas exposed for contact with a body fluid. In this case, the multiple working electrode areas, the multiple counter electrode areas and the multiple reference electrode areas are arranged symmetrically relative to each other. In this manner, a symmetrical potential distribution is produced when an alternating current is applied to the sensor.

An in vivo sensor using multiple reference electrode areas that are exposed for contact with body fluid in some cases may introduce cytotoxicity issues if all of such reference electrode areas include silver silver/chloride (Ag/AgCl), which is otherwise a preferable composition for reference electrodes. Surprisingly, however, it has been found that it is not necessary that all of the exposed reference electrode areas in such a multiple areas sensor include Ag/AgCl when they are electrically connected to one another. Instead, an electrode of a non-corroding conductive material, such as exposed gold or palladium or carbon is capable of sensing the potential at a particular position and providing the necessary feedback to a potentiostat or other device to enable potentiostatic control of the sensor.

In another embodiment, an electrochemical biosensor for testing a body fluid is provided. The sensor includes a substrate, a working electrode formed on or in the substrate, a counter electrode formed on or in the substrate and a reference electrode formed on or in the substrate that includes multiple analyte sensitive reference electrode areas that are exposed for contact with body fluid. In this sensor at least one of the multiple reference electrode areas comprises a different material composition than the remaining reference electrode areas. More particularly, the at least one of the multiple reference electrode areas comprises Ag/AgCl and the remainder of the areas comprise a non-corroding conductor, such as gold, platinum or carbon.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein:

FIGS. 2A and 2B are graphs showing impedance magnitude and phase, respectively, over time for the sensor depicted in FIGS. 1A and 1B;

FIG. 2C is a graph of potential versus location for the sensor depicted in FIGS. 1A and 1B;

FIG. 3A is a perspective view of an in vivo sensor;

FIGS. 4A and 4B are graphs showing impedance magnitude and phase, respectively, over time for the sensor depicted in FIGS. 3A and 3B;

FIG. 4C is a graph of potential versus location for the sensor depicted in FIGS. 3A and 3B;

FIG. 7A is an enlarged fragmentary plan view of another in vivo sensor embodiment;

FIG. 7B is an enlarged fragmentary plan view of the sensor of FIG. 7A illustrating different features;

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present embodiments.

Figure 1A:
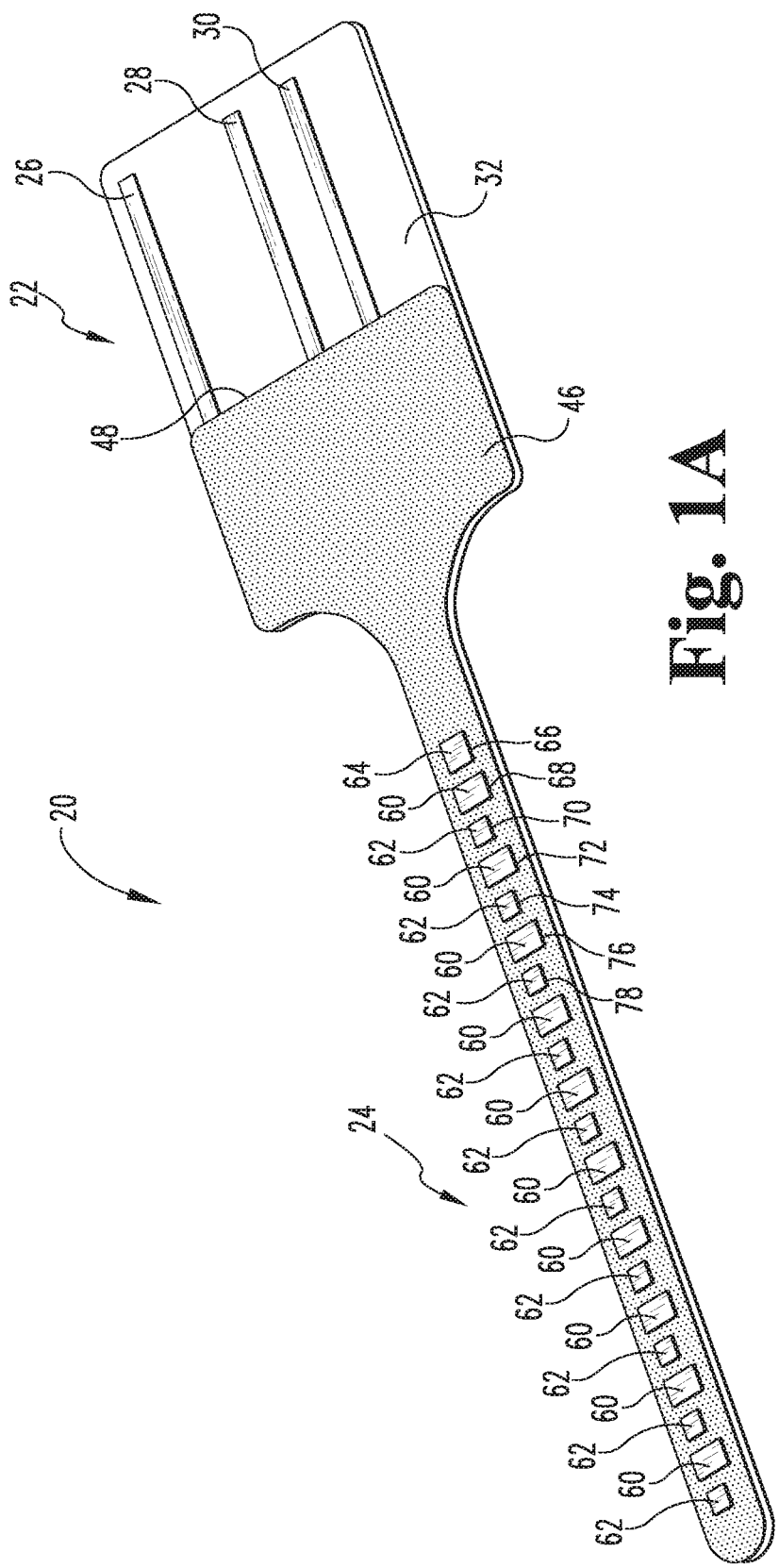
FIG. 1A is a perspective view of an in vivo sensor.
Figure 1B:
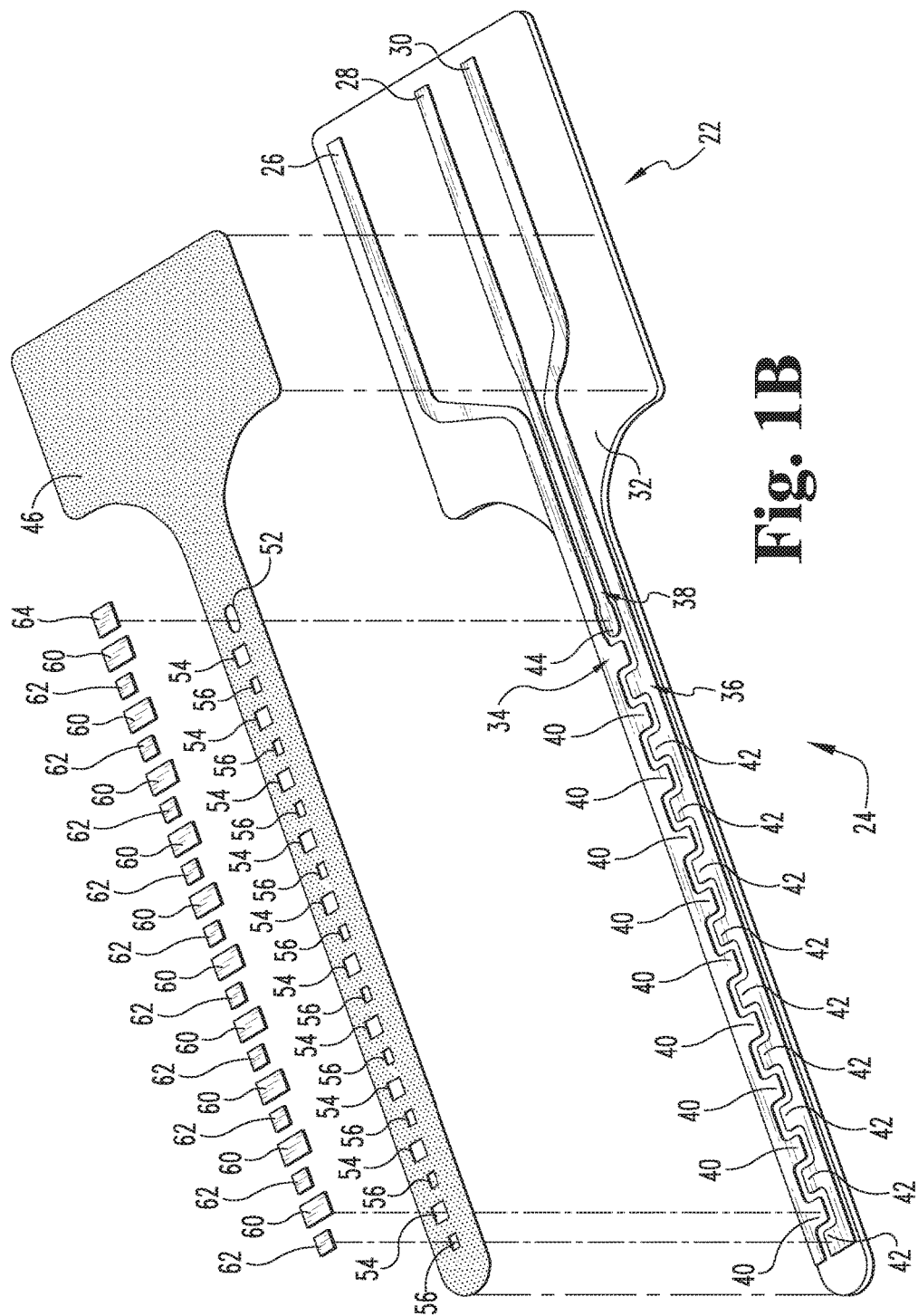
FIG. 1B is an exploded perspective view of the in vivo sensor of FIG. 1A.

Turning now to FIGS. 1A and 1B, the components of a sensor according to one embodiment are shown. In vivo sensor 20 has contact portion 22 and body portion 24. Contact portion 22 includes contacts 26, 28, and 30 for electrical connection to a volt meter, a potentiostat, an ammeter, and/or other detection or display components. The contacts may be directly or indirectly connected with such devices which control the potential or current in the sensor and receive and evaluate the electrical signal from the sensing portion of the sensor, as is well known in the art of electrochemical biosensors.

As can also be seen in FIGS. 1A and particularly 1B, sensor 20 includes a base substrate 32 which comprises an insulating material supporting the electrode system and other components. Typically, plastics such as vinyl polymers, polyimides, polyesters, and styrenes provide the electrical and structural properties which are required. Further, because the sensor in certain embodiments may be mass producible from rolls of material, it is desirable that the material properties be appropriate to have sufficient flexibility for roll processing, while also giving a useful stiffness to the finished sensor. The base substrate can be selected as a flexible polymeric material such as polyester, especially high temperature polyester materials; polyethylene naphthalate (PEN); and polyimide, or mixtures of two or more of these. Polyimides are available commercially, for example under the trade name Kapton®, from E.I. duPont de Nemours and Company of Wilmington, Del. (duPont). A particularly suitable base substrate material is MELINEX® 329 available from duPont.

The embodiment illustrated in FIGS. 1A and 1B utilizes a three-electrode system including a counter electrode 34 connected to contact 26, working electrode 36 connected to contact 30 and reference electrode 38 connected to contact 28. The electrodes and the electrode system may be formed from a variety of materials as known in the art. The electrodes should be non-corroding electrical conductors that have a relatively low electrical resistance and are electrochemically inert over the operating range of the sensor. Suitable conductors for the working electrode include gold, palladium, platinum, carbon, titanium, ruthenium dioxide, and indium tin oxide, and iridium, as well as others. The counter electrode may be made of the same or different materials. Similarly, the reference electrode may comprise the same materials and may also include silver/silver chloride. The electrodes may be applied to the base substrate in any fashion that yields electrodes of adequate conductivity and integrity. Exemplary processes are well known in the art, and include, for example, sputtering, printing, etc. In one embodiment, gold electrodes are provided by coating the base substrate and then removing selected portions of the coating to yield the electrode system. Any conventional technique may be used to selectively remove areas of the deposited film to define the electrical contacts and electrodes, and examples of such conventional techniques include, but are not limited to, laser ablation, chemical etching, dry etching, and the like.

The working and counter electrodes 34 and 36 of sensor 20 depicted in FIGS. 1A and 1B each have multiple exposed electrode areas. These areas are formed in part by the conductive portion of the electrodes as shown in FIG. 1B, in which the counter electrode 34 includes several counter electrode segments 40 that are interdigitated with similar working electrode segments 42. A single reference electrode segment 44 is defined at the end of the reference electrode conductor and is followed by ten pairs of counter electrode 40 and working electrode 42 segments, respectively.

With further reference to FIGS. 1A and 1B, a cover or insulating film 46 overlies the base substrate and electrode pattern. Cover 46 is applied to the substrate by printing, e.g., screen printing. Suitable materials for the cover layer include SD 2460/201, available from Peters, and laminated polyester with adhesive, photoimagable polyimide, sold under the trade names Pyralux or Vacrel from DuPont. Cover 46 has a top end or edge 48 that terminates short of the end of the sensor, thereby leaving contacts 26-30 exposed for contact with a meter or other device, as described above. Further, cover film 46 has openings that are sized and located to expose selected portions of the working, counter and reference electrode segments. In the embodiment illustrated in FIG. 1B, opening 52 exposes reference electrode segment 44, openings 54 expose counter electrode segments 40, and openings 56 expose working electrode segments 42.

In some embodiments, a conductive material may be applied over the openings 52, 54 and 56 and defines, in combination with the conductive segments, electrode areas that are exposed to body fluid, e.g., interstitial fluid, when the sensor is inserted subcutaneously into the skin. The composition of the conductive material depends upon design considerations and whether the conductive segment being covered is part of the working, counter, or reference electrode. Optionally, and as described below, it is possible that one or more of the conductive segments is not covered but is instead exposed for contact with body fluid. When a conductive material is used to cover electrode segments, it electrically contacts the segments of the working, counter or reference electrodes, as the case may be, through the openings in the cover film 46.

In one embodiment, the counter electrode covers or "spots" 60 shown in FIG. 1 can be formed of a carbon paste material that is applied in the location of openings 54 over film 46. The method of applying covers 60 can be, e.g., a conventional printing technique as known in the art. The covers are depicted in FIG. 1A and rectangular, but they may be formed as other shapes, e.g., round, oval, etc.

The covers 62 for the working electrode segments may also be formed of a carbon paste material, but typically also include a reagent for reaction with the body fluid. One example of the material for covers 62 is a conductive carbon ink formulation (e.g., PE401 carbon paste available from Acheson Colloids), manganese dioxide, and a solvent such as butyl glycol that is dispensed onto the working electrode segments 42 through openings 56. It will be appreciated that other conventional reagent layers may alternatively or additionally be formed on the working electrode areas. It is also possible in certain embodiments that conductive carbon would not be used and instead a conventional glucose oxidase formulation can be dispensed onto the working electrode segments 42. It is also possible to form a reagent layer on the counter electrode segments, which reagent may or may not be identical to the reagent layer formed on the working electrode segments. Other possible variations for conductive materials suitable for covers or spots for the electrode segments of sensors in accordance with these teachings are disclosed in incorporated by reference U.S. Publication No. 2008/0214910 and reference is made thereto.

Further, although not specifically illustrated, in vivo sensors in accordance with these teachings may include one or more additional layers to, e.g., limit diffusion of enzymes from the working electrode areas, limit diffusion of analyte to the working electrode reagent layer, hinder or resist absorption of protein, or the like. Such layers or membranes may include conventional hydrophilic polyurethane, methacryloyloxyethyl phosphorylcholine-co-butyl methacrylate (MPC) or the like. One example of a hydrophilic polyurethane that may be used to form such a resistive layer is described in U.S. Pat. No. 6,509,148 to Cha et al., the disclosure of which is incorporated herein by reference. An example of a commercially available MPC that may be used to form a resistive layer is available from NOF Corporation of Tokyo, Japan and marketed under the trademark LIPIDURE®. Other options and variations for diffusion limiting and other membranes suitable for sensors in accordance with these teachings are disclosed in incorporated by reference U.S. Publication No. 2008/0214910 and reference is made thereto. Further details and options concerning the architecture, membranes and other features of the sensor depicted in FIGS. 1A and 1B can be found in WO 2010/028708, which is hereby incorporated herein by reference in its entirety.

Cover or "spot" 64 which is deposited over opening 52 and electrically contacts reference electrode segment 44 may be formed from a conventional silver/silver chloride ink formulation, e.g., Ercon DPM 68.

As shown in FIG. 1A, the sensor 20 body portion 24 includes multiple distributed analyte sensitive areas, or areas, that are coextensive with the location of conductive covers 60, 62 and 64. Thus, FIG. 1A shows exposed reference electrode area 66, exposed working electrode area 68 and exposed counter electrode area 70. The areas then repeat in a pattern of working electrode area 72, counter electrode area 74, working electrode area 76, counter electrode area 78, and so on. As can be appreciated, all working electrode areas are connected to each other in parallel toward the contact portion 22 of the sensor, as are the counter electrode areas. Each area can be thought of as part of one or more electrochemical cells. For example, reference electrode area 66, counter electrode area 68 and working electrode area 70 form one cell. Similarly, the same reference electrode area 66, counter electrode area 72 and working electrode area 74 form a second cell; and reference electrode area 66, counter electrode area 76 and working electrode area 78 form a third cell.

In use, electronic circuitry external to the human is used to control operation of the sensor by sending electrical signals to sensor electrodes and monitoring an electrochemical reaction that takes place between the fluid/tissue and the exposed electrode areas. Typically, a DC voltage is applied across the working and counter electrodes and the resulting DC current that flows between the electrode areas can be correlated to the concentration of analyte, as is known in the art. It has been determined that for DC measurements of the kind just mentioned, the arrangement of multiple electrode areas shown in FIGS. 1A and 1B is superior to a sensor with a single small analyte sensitive area. It is believed that using multiple areas creates somewhat of an averaging effect and can correct for heterogeneities with respect to location and time that occur in the subcutaneous tissue in which the sensor is implanted. As such, the resulting DC measurements made with such a sensor 20 are more consistent and robust than with a conventional single area sensor. However, as noted above, it is also desirable to improve sensor performance by using AC signals to determine a complex impedance of the sensor, as described in U.S. Publication No. 20080214910, incorporated above by reference. As noted, complex impedance can be used to improve sensor performance by, e.g., enabling correction for changes in membrane permeability, sensor sensitivity drift, and to provide failsafes for sensor performance. As specifically described in U.S. Publication No. 2008/0214910, the undesirable variations sought to be minimized within a tolerable level, or at least reduced as just described, may be or include, for example, but are not limited to, sensor sensitivity drift over time, sensor offset drift over time, sensor signal sensitivity and/or offset variations during an initial break-in period of the sensor 10, anomalies present in the sensor signal and/or in sampled sensor signal data, and the like.

Use of such AC signals with a sensor 20 such as depicted in FIGS. 1A and 1B has been found unworkable. Without wishing to be tied to any specific theory, it is believed that sensors with multiple sensitive areas can cause the surrounding environment, the sensed volume, to have a very complex potential distribution compared to sensors with a single sensitive area. This complexity depends upon the conductivity of the environment, the amount of current passed by the sensor, and the location and impedance of the counter electrode(s) and the reference electrode(s), among other things. It has been found that the multiple exposed analyte sensitive area sensor arrangements such as the one shown in FIG. 1 are not suitable for making AC measurements. The complex potential distribution and the changing impedance of the counter electrodes make the measured impedance values unstable, and can introduce unwanted features, or "artifacts," into the impedance spectrum.

For example, FIGS. 2A and 2B plot impedance magnitude and phase, respectively, over time, for the sensor depicted in FIGS. 1A and 1B at 100 kHz, 10 kHz and 1 kHz when measured for two days in an aqueous glucose solution. As shown, the impedance changes in a rather arbitrary and chaotic manner, especially just beyond t=100 and between 250 and 300.

These arbitrary and chaotic impedance changes are believed to be attributable at least in part to the placement of the reference electrode in the array. To illustrate, FIG. 2C is a graph formed by finite element modelling (electrostatic model) showing the relative magnitude of the potential with respect to location along the sensor embodiment of FIGS. 1A and 1B at peak voltage when an AC signal is applied to the sensor. Arrow 202 shows the potential at the location of exposed reference electrode area 64. Areas 204 (zero potential) are the working electrode areas and areas 206 are the counter electrode areas. As can be appreciated, the slope or gradient of the potential at area 202 is significant and even varies across area 64 from edge to edge in the lengthwise direction of the sensor. The steep slope at location 202 of the reference electrode area 64 is believed to cause instability when using AC measurements with the sensor.

Testing has shown that positioning the exposed reference electrode area at the distal end of the sensor, e.g., at the location of arrow 208, results in similar drawbacks. As can be seen from FIG. 2C, moving the reference electrode closer to the last working electrode desirably brings the potential of the reference closer to that of the working electrode but it also undesirably positions the reference electrode in a location with a larger potential gradient. Thus, positioning the reference electrode at the ends of the array introduces, on the one hand, the problem of sensing an inaccurate potential if the reference electrode location is remote from the working electrode. This can be appreciated, for example, with reference to the two different potentials indicated in FIG. 2C at locations 202 and 208, which are on opposite ends of the array. On the other hand, if the reference electrode area is positioned close to the working electrode, the resulting measurements can be unstable or unreliable due to the reference electrode exposed area being positioned in an area of large potential gradient.

Figure 2D:
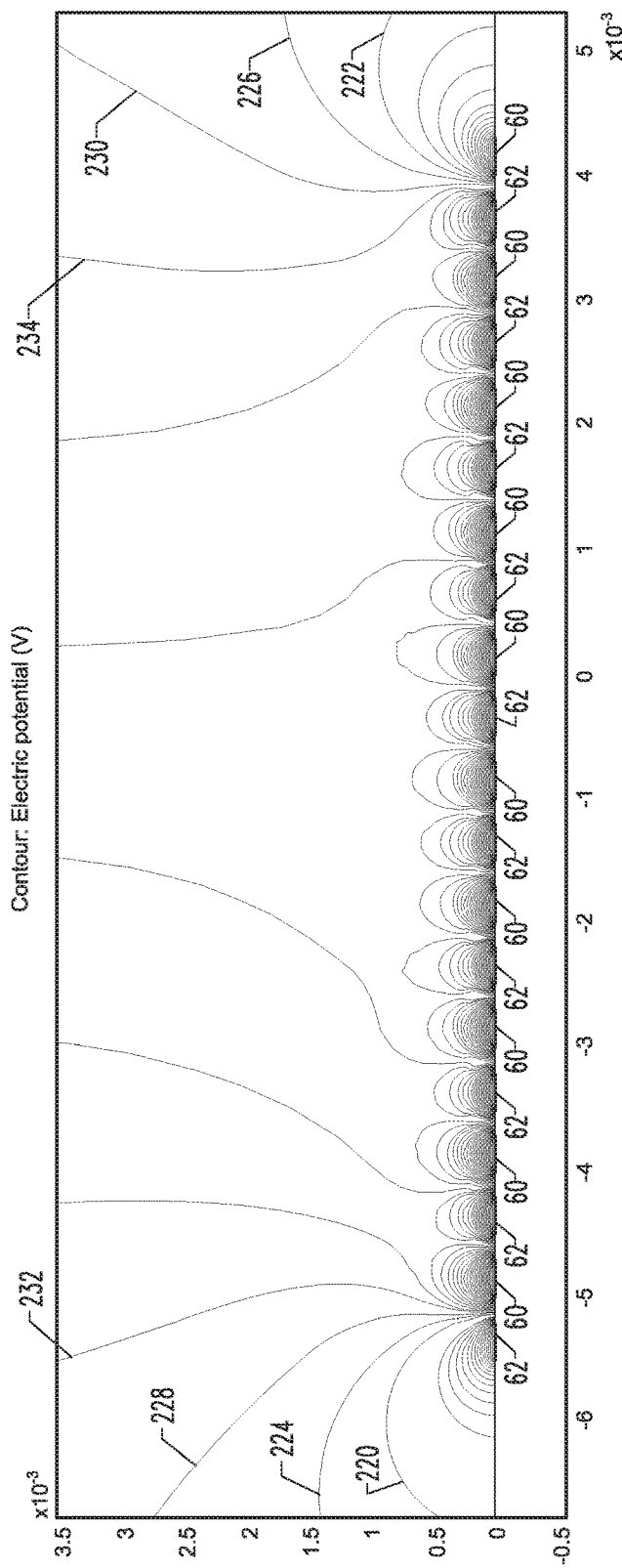
FIG. 2D is a schematic electric field line diagram for the sensor depicted in FIGS. 1A and 1B.

The asymmetry of the potential distribution of the sensor embodiment of FIGS. 1A and 1B can be further appreciated with reference to the electric field diagram shown in FIG. 2D. As was the case with the graph of FIG. 2C, the model used to create the electric field diagram of FIG. 2D is based on peak voltage when an AC signal is applied to the sensor. The electric field can be thought of as a measure of the change in potential from point to point along the array. The strength of the electric field is represented in FIG. 2D as proportional to the number of lines per unit area. The positions of the counter and working electrode exposed areas 60 and 62 are shown. A comparison of the magnitude of the potential of electric field lines at opposite and complementary positions on the array illustrates the asymmetry of the potential distribution of this sensor embodiment. For example, field lines 220 and 222 are positioned at opposite and complementary positions on the sensor array and have substantially different potentials. The same holds true, e.g., for the following pairs of field lines: 224/226; 228/230 and 232/234. These asymmetric aspects of the potential distribution are believed to contribute to the instability of sensor 20 when using AC measurements.

Figure 3B:
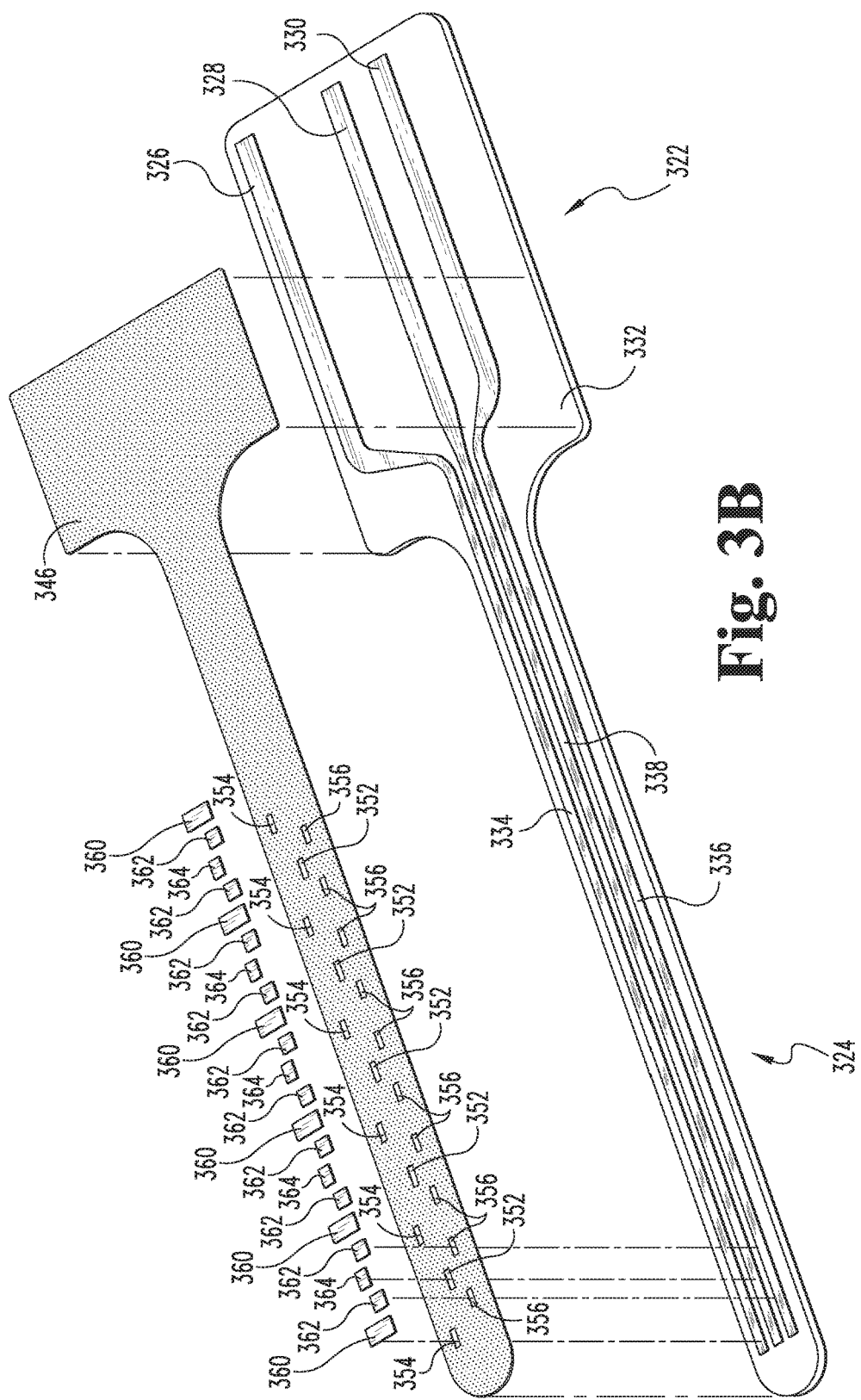
FIG. 3B is an exploded perspective view of the in vivo sensor of FIG. 3A.

Turning now to FIGS. 3A and 3B, a second in vivo sensor embodiment is shown that addresses the chaotic impedance changes resulting from applying AC measurements to a multiple electrode area sensor. Sensor 320 has contact portion 322 and body portion 324. Contact portion 322 includes contacts 326, 328, and 330 formed on base substrate 332, as described above.

Like sensor 20 discussed above, sensor 320 also utilizes a three-electrode system including a counter electrode 334 (top in FIG. 3B) connected to contact 326, working electrode 336 (bottom in FIG. 3B) connected to contact 330 and reference electrode 338 (center in FIG. 3B) connected to contact 328. As shown, the electrodes are formed as substantially parallel traces extending along the lengthwise direction of the sensor. The electrodes and the electrode system may be formed from a variety of materials as known in the art and as described above in more detail with reference to sensor 20.

Unlike the sensor embodiment of FIG. 1, the shape of the conductive portion of the electrodes formed on substrate 332 does not change in the locations of the exposed electrode areas for sensor 320. Instead, the placement and size of the electrode areas are determined by the positions of the openings formed in insulating film 346 and the associated conductive covers or spots that are placed over the openings in the film. More specifically, with reference to FIG. 3B, counter electrode covers or spots 360 are placed over openings 354 to form multiple counter electrode areas. As shown, the size of the spots or covers 360 that define the counter electrode areas are made significantly larger than the width of the electrode. With this arrangement, the shape of the conductive traces overlying substrate 332 does not dictate the shape, size or exact position of the exposed electrode areas. The counter electrode covers 360 can be formed, e.g., from a carbon paste, as described above.

With further reference to FIG. 3B, working electrode covers 362 are placed over openings 356 in the manner just discussed. As discussed above, covers 362 for the working electrode areas may be formed, e.g., of a carbon paste material which includes a reagent for reaction with the body fluid. Sensor 320 has multiple exposed reference electrode areas, the significance of which is discussed in more detail below. Reference electrode covers 364 are placed over openings 352 in the manner just discussed to form multiple reference electrode areas.

Referring to FIG. 3A, sensor 320 has a substantially linear array of five electrochemical cells: 380, 382, 384, 386 and 388. Each cell has one reference electrode area 366, two counter electrode areas 368 and two working electrode areas 370. In the interior adjacent cells, a counter electrode area is shared. For example, cells 380 and 382 share a counter electrode area therebetween as do cells 382 and 384. In another variation of this embodiment, however, it would be possible to divide the interior counter electrode areas into two separate counter electrode areas so that no exposed electrode areas are shared among cells.

Quite remarkably, it has been found that the potential distribution in the environment of the sensor for this embodiment is much more symmetric and homogeneous than with the arrangement of sensor 20 shown in FIG. 1A. FIGS. 4A and 4B depict impedance magnitude and phase, respectively, over time, for a sensor as depicted in FIGS. 3A and 3B at 100 kHz, 10 kHz and 1 kHz when measured for two days in an aqueous glucose solution. Unlike the plots shown in FIGS. 2A and 2B, the impedance plots in FIGS. 4A and 4B are relatively smooth, with no unwanted spikes or other chaotic changes. Incidentally, the plots in FIGS. 4A and 4B resemble impedance plots that are obtained in applying AC currents to a sensor with a single exposed electrode area. Sensor 320 is thus suitable for use with AC measurements (e.g., as set forth in U.S. Publication No. 2008/0214910) to determine useful information about the sensor, e.g., membrane permeability and sensor status.

Figure 4D:
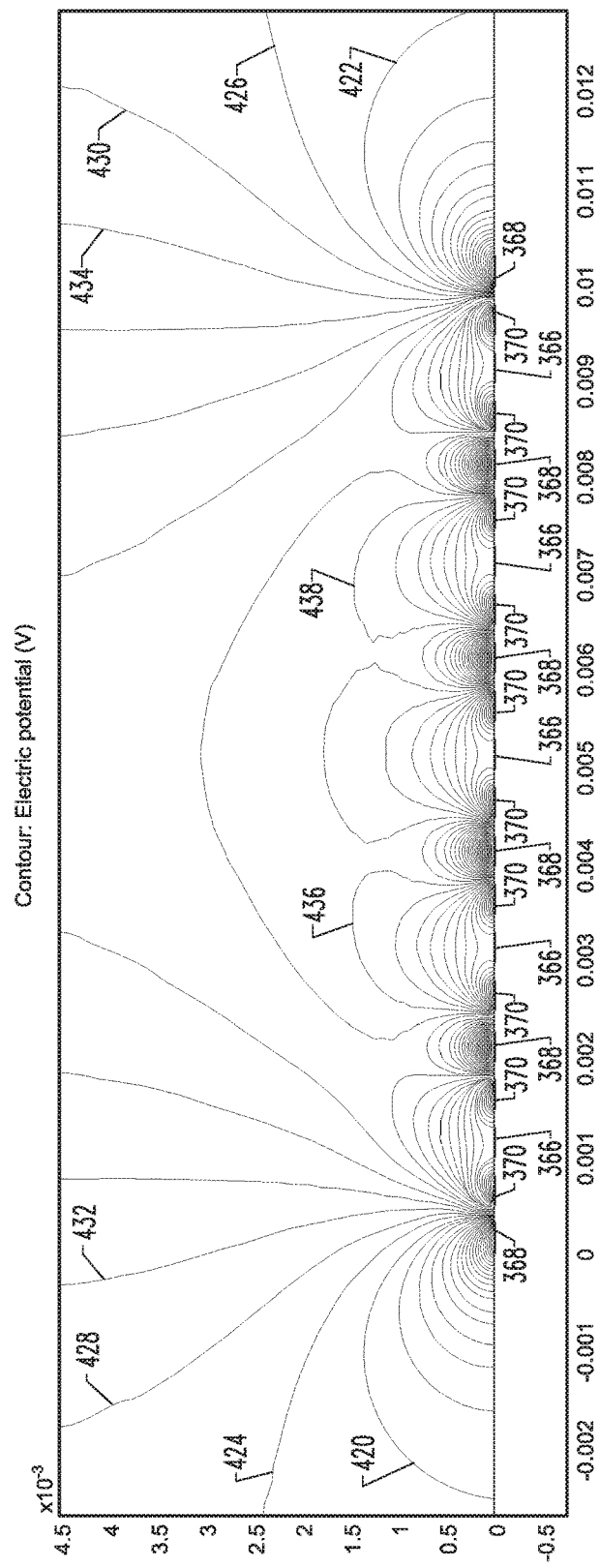
FIG. 4D is a schematic electric field line diagram for the sensor depicted in FIGS. 3A and 3B.

The symmetry of the arrangement can be appreciated with reference to FIGS. 4C and 4D. FIG. 4C is a graph formed by finite element modelling (electrostatic model) showing the relative magnitude of the potential with respect to location along the sensor embodiment of FIGS. 3A and 3B at peak voltage when an AC signal is applied to the sensor. The potential values in the areas of the reference electrode exposed areas 366 (see FIGS. 3A and 3B) are shown at reference numerals 402. Working electrode exposed areas 370 are shown at reference numerals 404 and counter electrode exposes areas are shown at reference numerals 406. It can be appreciated that the potential at all reference electrode areas 402 is substantially the same. Further, the shape of the potential distribution overall in the graph of FIG. 4C is symmetric. For example, the potential on opposite sides of the array at areas 410 and 412 is substantially the same, quite unlike the model shown in FIG. 2C. Still further, the difference between the potential at the reference electrode areas 402 and at the working electrode areas 404 is substantially the same across the array. Importantly, there are flat spots on the reference electrode areas 402 such that exposed reference electrode areas positioned in areas 402 produce reliable and stable values.

The symmetry can be further appreciated with reference to FIG. 4D, which is a diagram showing equi-potential electric field lines at peak voltage for the sensor embodiment of FIGS. 3A and 3B with an AC signal applied to the sensor. The locations of the exposed electrode areas 366, 368 and 370 are shown. As noted above, the electric field can be thought of as a measure of the change in potential from point to point along the array, and the strength of the electric field is represented in FIG. 4D as proportional to the number of lines per unit area.

It should be appreciated from FIG. 4D that the potential gradient around counter and working electrode exposed areas 368 and 370, respectively, is quite high, as indicated by the high density of field lines positioned over these areas. By contrast, the field line density above reference electrode exposed areas 366 is sparse, which indicates that the potential gradient above the reference electrode areas is small. The electric field lines in FIG. 4D thus present another way of appreciating the "flat spot" in potential gradient at the position of the reference electrodes, which is believed to contribute to the ability to use the inventive sensor disclosed herein with AC signals applied thereto.

The symmetry of the potential distribution of the sensor embodiment of FIGS. 3A and 3B can be further appreciated by a comparison of the potential of complementary field lines shown in FIG. 4D. Specifically, field lines 420 and 422 on opposite sides of the array have substantially the same potential. The same holds true, e.g., for the following pairs of field lines: 424/426; 428/430; 432/434 and 436/438. Generally, the potential measured on one side of the array will be substantially the same as the potential measured at a corresponding but opposite side of the array in a symmetric arrangement as depicted in FIGS. 4C and 4D. FIGS. 4C and 4D exemplify a symmetric potential distribution, as that term is understood in this disclosure. Other sensors having symmetrical arrangements of exposed electrode areas are disclosed below.

To further explain the symmetrical arrangement of exposed electrode areas, and again not wishing to be tied to any specific theory, it is believed that when using a DC current with a multiple analyte sensitive area sensor, what is measured can be thought of as the sum of the currents through the individual electrode areas. However, with AC currents, there are phase differences that do not occur in DC measurements and the peak current level can be very high. The contribution of the measurement of the individual electrode areas depends upon the impedance between each electrode area and all of the other electrode areas, and this varies with time as the characteristics of the electrode areas and surrounding tissue change. That is, in an array of many exposed electrode areas, a given change in impedance in one electrode area at one position in the array may have a different effect on the total signal than the same change on an electrode area at a different position in the array, such that it is not clear exactly what combination is being measured at any one time. This is believed to cause the chaotic and arbitrary impedance changes shown in FIGS. 2A and 2B for sensor 20.

Surprisingly, however, sensor 320 shows that by arranging the multiple areas symmetrically, the impedance measurements can be greatly improved. As used in this specification, the terms "symmetrically," "symmetrical," "symmetric" and variations of these terms should be construed broadly. For example, it can said for the embodiment shown in FIG. 3A that the term "symmetrical" generally covers an arrangement in which the relative location or physical relationship among the exposed counter electrode areas, exposed reference and exposed working electrode areas results in a symmetric potential distribution, e.g., like the one depicted in FIGS. 4C and 4D.

Generally, a symmetrical arrangement of electrode areas is one which the multiple electrode areas are arranged relative to each other in such a way that a symmetrical potential distribution is produced when an AC signal is applied to the sensor and that the exposed working electrode areas all have substantially the same potential. A symmetrical potential distribution is one in which the impedance magnitude and phase over time are substantially stable and substantially free of unwanted spikes or other chaotic changes such as those depicted in FIGS. 2A and 2B for sensor 20. As noted above, a symmetrical potential distribution is necessary in order to use the sensor with AC measurements.

By contrast, an arrangement that would not be considered "symmetrical" in accordance with these teachings is sensor 20 shown in FIG. 1. Returning to FIG. 1A, it can be appreciated that the relationship of the counter electrode areas and working electrode areas to the single reference electrode area is different in each cell. In the case of sensor 20, the distance between the single reference electrode area and the multiple counter and working electrode areas increases as one traverses the lengthwise direction of the sensor toward its tip. It is believed that this asymmetry of the reference electrode area relative to the working and counter electrode areas contributes to the chaotic impedance readings that are obtained when attempting to use such sensor 20 with AC currents. This is further shown by the asymmetric potential distribution and electric field line diagram illustrated in FIGS. 2C and 2D, respectively.

This is not to say that the term "symmetrical" for purposes of these teachings requires that the exposed electrode areas are identical in all cells. Indeed, as shown in FIG. 3A, the counter electrode areas at the ends of the array form part of only one cell, whereas the interior counter electrode areas are shared between adjacent cells. The arrangement of electrode areas in sensor 320 is nonetheless symmetrical, as the term is used in these teachings. As mentioned above, a modification to sensor 320 which would also be symmetrical would be to divide the shared counter electrode areas in the center of the array into two separate, spaced areas such that no electrode areas were shared among any of the cells. Nonetheless, an arrangement in which an electrode area is shared among one or more cells can provide excellent impedance measurements and is thus considered symmetrical. Further, as discussed in detail below, exposed electrodes areas of one type, e.g., reference electrode areas, can be formed from different compositions and still be part of a symmetrical arrangement of electrode areas in accordance with these teachings.

Figure 5A:
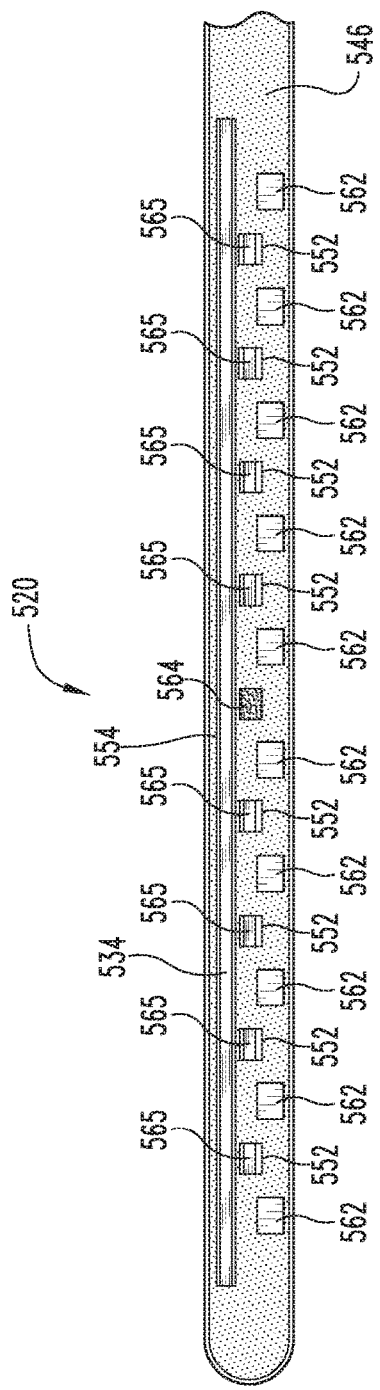
FIG. 5A is an enlarged fragmentary plan view of another in vivo sensor embodiment.
Figure 5B:
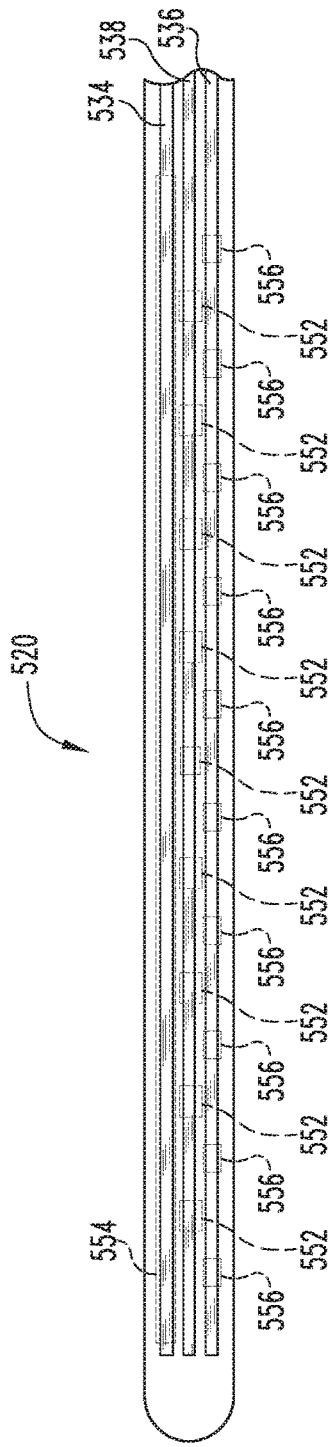
FIG. 5B is an enlarged fragmentary plan view of the sensor of FIG. 5A illustrating different features.

As another example of electrode areas being shared amongst cells, FIGS. 5A and 5B show a sensor 520 having a single counter electrode area that extends along the lengthwise direction of the sensor. FIG. 5A is an enlarged fragmentary plan view and FIG. 5B is a similar view except with cover 546 removed to show the electrode conductor material. As with the embodiment illustrated with reference to FIGS. 3A and 3B, the electrodes are formed as substantially parallel traces, namely, counter electrode trace 534, working electrode trace 536 and reference electrode trace 538 as shown in FIG. 5B. Openings 552 are formed in film 546 to define the locations of the reference electrode areas that will be exposed to body fluid whereas openings 556 shown in dashed lines in FIG. 5B are formed for the working electrode areas. The counter electrode area is defined by an elongated opening 554 that extends along the lengthwise direction of the sensor 520 and exposes the counter electrode conductor material 534.

The counter electrode area in this embodiment is shown as uncovered, being either exposed gold or palladium in prototypes that were assembled and tested. This was done as a result of tolerance considerations in a prototype production process. It is envisioned, however, that in mass-produced sensor embodiments, the single elongated exposed counter electrode area defined by opening 554 shown in FIG. 5A would instead be covered with, e.g., a carbon paste, as described above, which would serve to lower the impedance of the counter electrode. In turn, this would reduce the need for a high potential to supply the necessary current and would further in turn reduce the possibility of the sensor failing.

The working electrode areas 562 are formed of a carbon paste and reagent described above with reference to the sensor embodiments of FIGS. 1 and 3. Eight of the nine reference electrode areas 565 are exposed through the windows 552 formed in film 546 but are otherwise uncovered, as shown in FIG. 5A. The central reference electrode area 564 is covered with a silver/silver chloride material as described above. This use of different materials for electrode areas in an array is another inventive aspect of these teachings, the significance of which is discussed below.

Figure 6A:
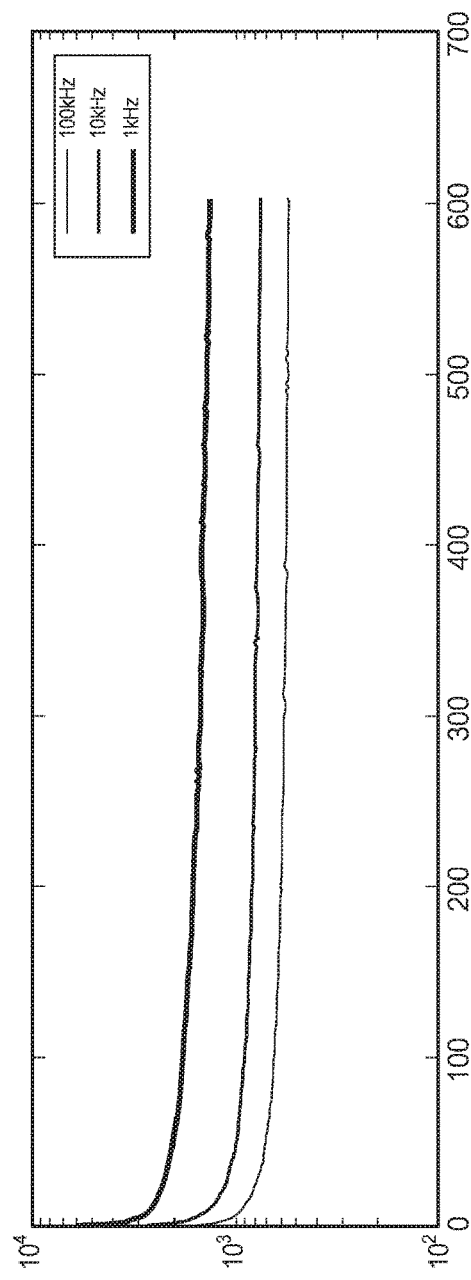
FIGS. 6A and 6B are graphs showing impedance magnitude and phase, respectively, over time for the sensor depicted in FIGS. 5A-5B.
Figure 6B:
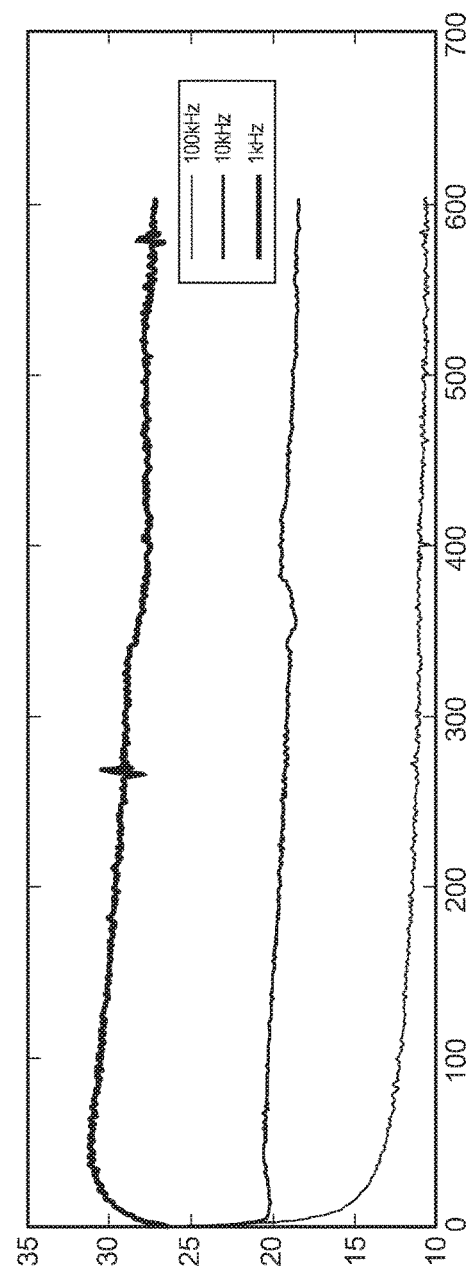

As can be appreciated, the arrangement shown in FIG. 5A is symmetrical in that the relative location or physical relationship of the counter electrode area (or portion thereof) to each working electrode area in the array of working electrode areas is substantially the same. The same can be said for the counter electrode area relative to each reference electrode area in the array of reference electrode areas. FIGS. 6A and 6B confirm the symmetry. FIGS. 6A and 6B depict impedance magnitude and phase, respectively, over time, for a sensor as depicted in FIGS. 5A-5B at 100 kHz, 10 kHz and 1 kHz when measured for two days in an aqueous glucose solution. The impedance plots in FIGS. 6A and 6B are relatively smooth, with no unwanted spikes or other chaotic changes. Sensor 520 is suitable for use with AC measurements as set forth in U.S. Publication No. 20080214910.

This symmetric potential distribution is achieved with sensor 520 even though one of the reference electrode areas has a different material composition than the other eight reference electrode areas. As can be appreciated, achieving the desired symmetrical potential distribution that enables the use of AC measurements in many sensor embodiments involves using several reference electrode areas. In single analyte sensitive area sensors, the reference electrode or at least the exposed portion thereof is typically produced with Ag/AgCl, which is a sparingly soluble salt which adopts a stable, known potential in the presence of a defined concentration of chloride ion. Silver ions, however, are mildly toxic and if present in sufficiently large amounts could possibly cause a sensor structure to fail cytotoxicity test requirements. The risk of not meeting cytotoxicity requirements is increased with the use of multiple reference electrode areas composed of Ag/AgCl. Such sensors may be unsuitable in an in vivo environment, especially in humans.

Quite surprisingly, however, it has been found that it is not necessary that all of the exposed reference electrode areas include Ag/AgCl when they are electrically connected to one another. An electrode of a non-corroding conductive material, such as exposed gold or palladium (areas 565 in FIG. 5A) or carbon is capable of sensing the potential at a particular position and providing the necessary feedback to the potentiostat to enable potentiostatic control of the sensor. In an associated group of reference electrode areas in which only one area 564 is covered with Ag/AgCl, the exposed areas 565 will be at the same potential that is supported by the Ag/AgCl covered area.

Again without wishing to be bound by any specific theory, the remarkable discovery just noted might be explained as follows. At high frequencies, e.g., greater than 10 Hz, it is important that the reference electrode impedance is small enough so that the potentiostat or similar device can provide the correct control signal to the sensor. The exposed areas 565 are suitable for sensing the potential at their location at high frequencies because areas 565 have a low impedance connection to the environment at high frequencies. On the other hand, at low frequencies, the exposed areas 565 have a very high impedance and therefore do not provide a good reference potential. However, at these lower frequencies, the potential distribution in the cell is more uniform and is adequately measured by the single Ag/AgCl reference electrode area 564. Thus, locating the single Ag/AgCl reference electrode area remote from several of the other working electrode areas 562 has been found to nonetheless result in a good reference potential at low frequencies, thus offsetting the deficiencies resulting from the high impedance of the exposed areas 565 at low frequencies. By using this inventive teaching of less than all and in some cases only one reference electrode area having Ag/AgCl, the inventive sensor has the advantages of multiple electrode areas in a symmetric arrangement, but is also biocompatible.

FIGS. 6A and 6B depict impedance magnitude and phase, respectively, over time, for a sensor as depicted in FIGS. 5A-5B at 100 kHz, 10 kHz and 1 kHz when measured for two days in an aqueous glucose solution. The impedance plots in FIGS. 6A and 6B are smooth, with no unwanted spikes or other chaotic changes. Sensor 520 is thus suitable for use with AC measurements as set forth in U.S. Publication No. 2008/0214910 to determine useful information about the sensor, e.g., membrane permeability and sensor status.

If only one reference electrode area having Ag/AgCl is to be used in a sensor, it is preferable to position such Ag/AgCl reference electrode area to minimize the distance between it and the farthest uncovered reference electrode areas. In the embodiment shown in FIG. 5A, the position for reference electrode area 564 is in the center of the array. Furthermore, it is envisioned that more than one, but less than all reference electrode areas might be formed from Ag/AgCl in other embodiments. One of skill in the art will readily recognize other suitable configurations.

Another example of a symmetrical arrangement of exposed electrode areas is shown in sensor 720 depicted in FIGS. 7A and 7B. The arrangement of electrode areas in sensor 720 is substantially the same as in sensor 320 described above with reference to FIGS. 3A and 3B. That is, openings 754 and 756 in film 746 allow cover material such as carbon paste and carbon paste/reagent to contact the counter and working electrodes 734 and 736, respectively, to form counter electrode areas 760 and working electrode areas 762, respectively. Similarly, openings 752 in film 746 define the reference electrode areas 765, which are also depicted in FIG. 7A as covered in a carbon paste.

Sensor 720 differs from sensor 320 in that sensor 720 employs only a single Ag/AgCl covered reference electrode area 764. The remainder of the reference electrode areas 765 are covered in a carbon paste, as just noted. It should be understood, however, that areas 765 could optionally be provided with no covering material, formed instead from the bare exposed conductor of the reference electrode, e.g., gold or palladium, as was the case with sensor 520. As was the case with sensor 520, the bare or carbon covered reference electrode areas 765 are capable of sensing the potential at high frequencies, but not at low frequencies. Nonetheless, the single Ag/AgCl reference electrode area 764 provides a good reference potential at low frequencies.

Figure 8A:
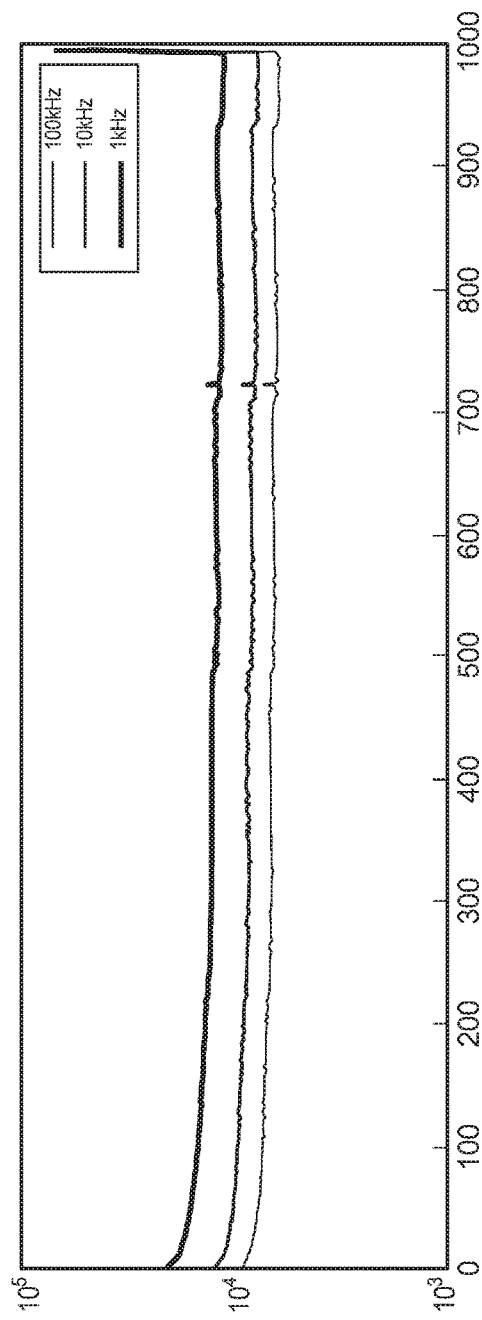
FIGS. 8A and 8B are graphs showing impedance magnitude and phase, respectively, over time for the sensor depicted in FIGS. 7A-7B.
Figure 8B:
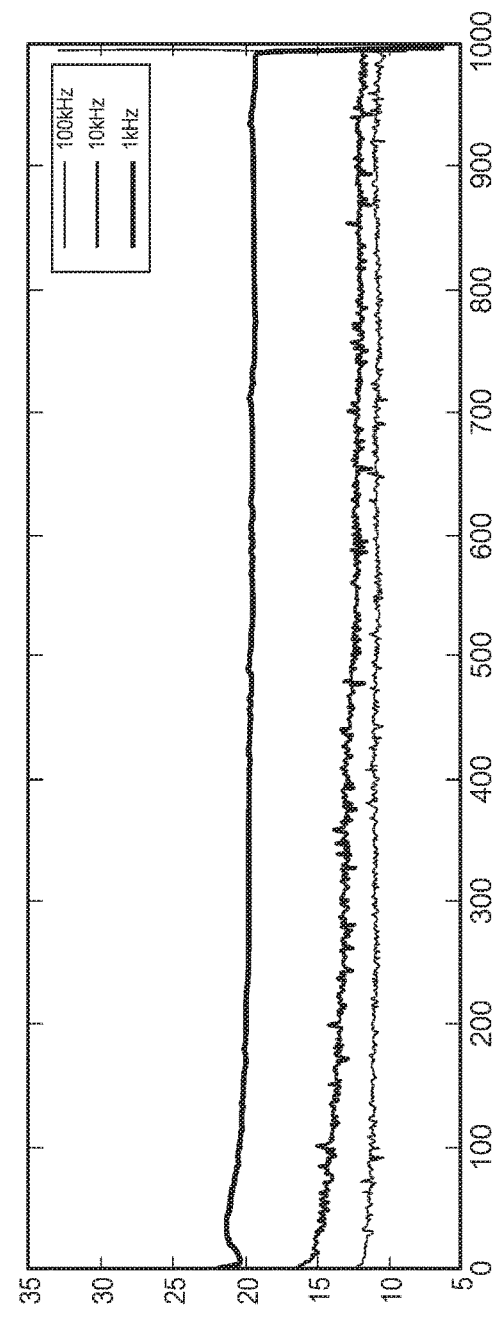

FIGS. 8A and 8B confirm that the potential distribution is symmetric. FIGS. 8A and 8B depict impedance magnitude and phase, respectively, over time, for a sensor as depicted in FIGS. 7A-7B at 100 kHz, 10 kHz and 1 kHz when measured for two days in an aqueous glucose solution. The impedance plots in FIGS. 7A and 7B are relatively smooth, with no unwanted spikes or other chaotic changes. Sensor 720 is suitable for use with AC measurements as set forth in U.S. Publication No. 2008/0214910, and, due to its limited use of Ag/AgCl, is biocompatible.

Figure 9:
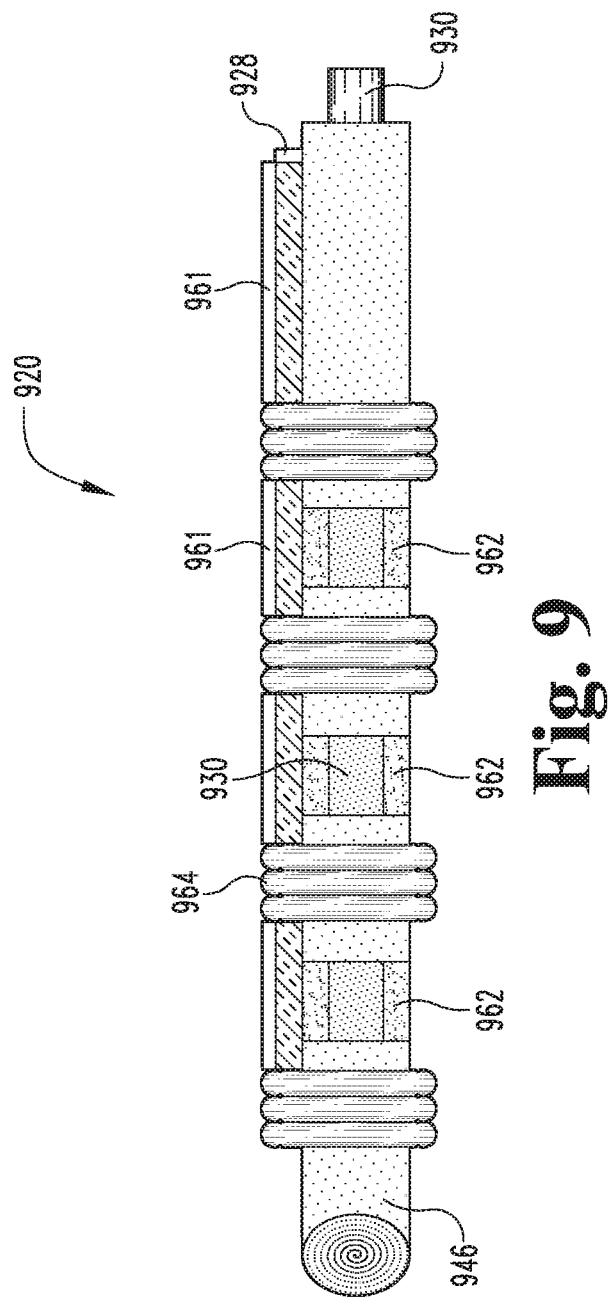
FIG. 9 is a view of another embodiment of an in vivo sensor.

While these teachings have been provided thus far in the context of a substantially planar sensor having multiple laminated layers, one of skill in the art should recognize that other sensor embodiments employing multiple exposed electrode areas can employ the inventive discoveries disclosed above. For example, FIG. 9 illustrates a cylindrical sensor 920 incorporating the symmetry principles taught above. A working electrode wire 930 is covered by insulating material 946 and has exposed areas 962 that include a reagent coating.

Sensor 920 is a two electrode system with a counter-reference electrode that serves the dual purpose of maintaining a reference potential and completing the electrical circuit. Counter-reference electrode connection wire 928 extends along the lengthwise direction of the cylindrical sensor and is covered by insulator 961. The counter-reference electrode wire 928 has four exposed portions, namely, counter-reference electrode areas 964 that are wrapped in a spiral around insulator 946. The exposed portions would be formed with Ag/AgCl, as discussed above. While the embodiment shown in FIG. 9 is prophetic and has not been tested, it is envisioned that sensor 920 would produce a symmetrical potential distribution due to the symmetrical arrangement of exposed analyte sensitive electrode areas. Sensor 920 is simply one example of how these teachings can be employed with various sensor embodiments. Thus, the cylindrical shape of the sensor 920 produces a cylindrically symmetrical or three dimensionally symmetric potential distribution. One of skill in the art would recognize other architectural variants in accordance with these teachings that could also produce a symmetrical distribution, e.g., placing electrodes on opposite sides of a planar substrate.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An electrochemical sensor for in vivo use, comprising:
   a substrate;
   a working electrode formed on or in the substrate and having multiple working electrode areas exposed for contact with a body fluid;
   a second electrode formed on or in the substrate and having at least one second electrode area exposed for contact with a body fluid; and
   the multiple working electrode areas and the at least one second electrode area comprising a symmetrical arrangement.

2. The electrochemical sensor of claim 1, wherein the application of the alternating current ("AC") signal is operable to correct for changes in membrane permeability, sensor sensitivity drift, or to provide fail safes for sensor performance.

3. The electrochemical sensor of claim 2, wherein the application of the AC signal is operable to correct for changes in sensor sensitivity drift.

4. The electrochemical sensor of claim 1, wherein a symmetrical potential distribution is produced when an AC signal is applied to the sensor.

5. The electrochemical sensor of claim 1, wherein the at least one second electrode area comprises multiple second electrode areas.

6. The electrochemical sensor of claim 1, wherein the second electrode comprises a reference electrode and the multiple second electrode areas comprise reference electrode areas exposed for contact with body fluid, the electrochemical sensor further comprising a counter electrode formed on or in the substrate, the counter electrode comprising at least one counter electrode area exposed for contact with body fluid.

7. The electrochemical sensor of claim 6, wherein the counter electrode comprises multiple counter electrode areas exposed for contact with a body fluid, wherein the multiple working electrode areas, the multiple counter electrode areas and multiple reference electrode areas are symmetrically arranged, wherein a symmetrical potential distribution is produced when an AC signal is applied to the sensor.

8. The electrochemical sensor of claim 7, wherein at least one of the multiple reference electrode areas comprises a different material composition than the remaining reference electrode areas.

9. The electrochemical sensor of claim 8, wherein the at least one of the multiple reference electrode areas comprises Ag/AgCl.

10. The electrochemical sensor of claim 9, wherein the remaining reference electrode areas comprise non-corroding electrical conductors.

11. The electrochemical sensor of claim 1, wherein the substrate is substantially planar.

12. The electrochemical sensor of claim 1, wherein the working electrode areas are spaced along a lengthwise direction of the sensor.

13. A method of applying AC signals to an in vivo electrochemical sensor, the sensor having a substrate, a working electrode formed on or in the substrate and a second electrode formed on or in the substrate, the method comprising:
  contacting the in vivo sensor with a body fluid, wherein multiple exposed areas of the working electrode contact the body fluid and wherein at least one exposed area of the second electrode contacts the body fluid;
  applying an AC signal to the sensor; and
  using the AC signal to correct for changes in membrane permeability, sensor sensitivity drift, sensor offset drift, or to provide fail safes for sensor performance.

14. The method of claim 13, wherein the application of the AC signal is used to correct for changes in sensor sensitivity drift.

15. The method of claim 13, wherein the application of the AC signal produces a symmetrical potential distribution.

16. The method of claim 13, wherein the second electrode comprises a reference electrode and the method further comprises exposing an exposed area of the reference electrode to the body fluid.

17. The method of claim 16, further comprising contacting an exposed area of a counter electrode of the sensor to the body fluid.

18. The method of claim 16, further comprising exposing multiple areas of the reference electrode to the body fluid.

* * * * *